United States Patent
Wingen et al.

(10) Patent No.: US 6,670,514 B2
(45) Date of Patent: Dec. 30, 2003

(54) FLUORINATED POLYCYCLES AND THEIR USE IN LIQUID-CRYSTAL MIXTURES

(75) Inventors: Rainer Wingen, Hattersheim (DE); Barbara Hornung, Hasselroth (DE); Wolfgang Schmidt, Dreieich (DE)

(73) Assignee: Clariant Finance (BVI) Limited (VG)

( * ) Notice: Subject to any disclaimer, the term of this patent is extended or adjusted under 35 U.S.C. 154(b) by 0 days.

(21) Appl. No.: 10/215,247

(22) Filed: Aug. 8, 2002

(65) Prior Publication Data

US 2003/0072894 A1 Apr. 17, 2003

(30) Foreign Application Priority Data

Aug. 16, 2001 (DE) .......................... 101 40 148

(51) Int. Cl.$^7$ .................... C07C 19/08; C07C 22/00; C07C 25/13; C07C 21/18; C07C 23/00
(52) U.S. Cl. ................. 570/129; 570/123; 570/124; 570/127; 252/299.01; 252/299.04; 349/1; 349/16; 349/12; 349/5
(58) Field of Search ................ 570/123, 124, 570/127, 129; 252/299.01, 299.04; 349/1, 16, 12, 5

(56) References Cited

U.S. PATENT DOCUMENTS

| | | | |
|---|---|---|---|
| 5,384,065 A | 1/1995 | Geelhaar et al. | 252/299.63 |
| 6,406,761 B1 | 6/2002 | Tarumi et al. | 428/1.1 |

FOREIGN PATENT DOCUMENTS

| | | |
|---|---|---|
| DE | 196 29 812 | 2/1997 |
| DE | 198 40 447 | 3/2000 |
| DE | 198 57 352 | 6/2000 |
| DE | 100 50 071 | 6/2001 |
| DE | 101 01 021 | 7/2002 |
| EP | 0 474 062 | 9/1992 |
| EP | 0 546 338 | 6/1993 |
| WO | WO 96/02485 | 2/1996 |
| WO | WO 99/58521 | 11/1999 |

OTHER PUBLICATIONS

English abstract for DE 19840447, Mar. 9, 2000, Ogawa, et al.
English abstract for DE 19857352, Jun. 15, 2000, Nonaka, et al.
English abstract for DE 10050071, Jun. 28, 2001, Yanai, et al.
Antony Blake, et al., Effects of Ligand Substituents (F for H; OR for R) on Mesogenic Properties on M(Salen) Derivative (M=Cu, Ni, VO). New Fluoro–Substituted Complexes and Crystal Structure of the Mesogen Ni(5–hexylSalen), Inorg. Chem., 1995, 34, pp. 1125–1129.
K. Ohmuro, et al., "33.3: Development of super–high–image–quality vertical–alignment–mode LCD", SID 97 Digest, pp. 845–848.
J.C. Jones, "Fast, high–contrast ferroelectric liquid crystal displays and the role of dielectric biaxiality", Displays, vol. 14, No. 2, 1993, pp. 86–93.
Mitsuhiro Koden, "Ferroelectric Liquid Crystal Materials For Practical FLCDs", Ferroelectrics, 1996, vol. 179, pp. 121–129.
Subodh Kumar, "A new and concise synthesis of 3–hydroxybenzo[c]phenanthrene and 12–hydroxybenzo[g]chrysene, useful intermediates for the synthesis of fjord–region diol epoxides of benzo[c]phenanthrene and benzo[g]chrysene", J. Org. Chem., 1997, 62, pp. 8535–8539.
Robert Aldred, et al., "Magnesium–mediated ortho–Specific formylation and formaldoximation of phenols", Chem. Soc. Perkin Trans. 1994, pp. 1823–1831.
Wilhelm F. Maier, et al., "Metamorphosis of palladium and its relation to selectivity in the rosenmund reaction", American Chemical Society, vol. 108, No. 10, 1986, pp. 2609–2616.
Yoichiro Nagai, "Hydrosilanes as reducing agents. A review", Org. Prep. Proc. Int. 12, 1980, pp. 15–48.
Organic Synthesis Coll. vol. 4, 1963, pp. 919–921.

*Primary Examiner*—Samuel Barts
*Assistant Examiner*—Elvis O. Price
(74) *Attorney, Agent, or Firm*—Alan P. Kass

(57) ABSTRACT

Compounds of the formula (I)

(I)

in which:
$R^1$ is H, F, $CF_3$, $OCF_3$, $OCF_2H$, $OCFH_2$, an alkyl radical or an alkenyl radical;
$R^2$ is H, an alkyl radical or alkyloxy radical or an alkenyl or alkenyloxy radical;
$G^2$—$G^1$ is —CH=CH—, —$CH_2CH_2$—, —CF=CH—, —CH=CF—, —CF=CF—, —$CH_2$—, —$CF_2$—;
$M^1$, $M^2$ are each, independently of one another, —C(=O)O—, —OC(=O)—, —$CH_2$O—, —O$CH_2$—, —$OCF_2$—, —$CF_2$O—, —C≡C—, —$CH_2CH_2$—, —$CF_2CF_2$— or a single bond;
$A^1$, $A^2$ are each, independently of one another, phenylene-1,4-diyl, unsubstituted, monosubstituted or disubstituted by F, cyclohexane-1,4-diyl, 1,3-dioxan-2,5-diyl;
m, n are each, independently of one another, zero or 1; m+n=0 or 1;

The invention furthermore provides a liquid-crystal mixture comprising one or more compounds of the formula (I) in an amount of 1 to 40% by weight, based on the liquid-crystal mixture and liquid-crystal displays containing this liquid-crystal mixture.

17 Claims, 1 Drawing Sheet

FLUORINATED POLYCYCLES AND THEIR USE IN LIQUID-CRYSTAL MIXTURES

More and more applications of LCDs—for example for use in automobiles, in which a temperature range from −40 to 100° C. can easily occur, but also for portable devices such as mobile telephones and notebook PCs, require liquid-crystal mixtures which have a very broad operating temperature range, but also a very low threshold voltage.

There is thus a continuing demand for novel, suitable liquid-crystal mixtures and liquid-crystal mixture components. As described by Ichinose et al. (IDW'00, Abstr. LCT4-3) or in DE-A-100 50 071, materials are sought which combine high optical anisotropy (Δn) and low rotational viscosity, with other parameters also being required, such as high absolute values of dielectric anisotropy (Δn) in addition to further application-relevant parameters.

It is therefore the object of the present invention to provide novel components for use in nematic or cholesteric or chiral smectic liquid-crystal mixtures which have high absolute values of dielectric anisotropy combined with a favorable viscosity/clearing point ratio. Moreover, the compounds should have a high light and UV stability and thermal stability. They should furthermore be suitable for realizing high voltage holding ratios (VHR). They should also be readily obtainable synthetically and thus potentially inexpensive.

Figure 1:
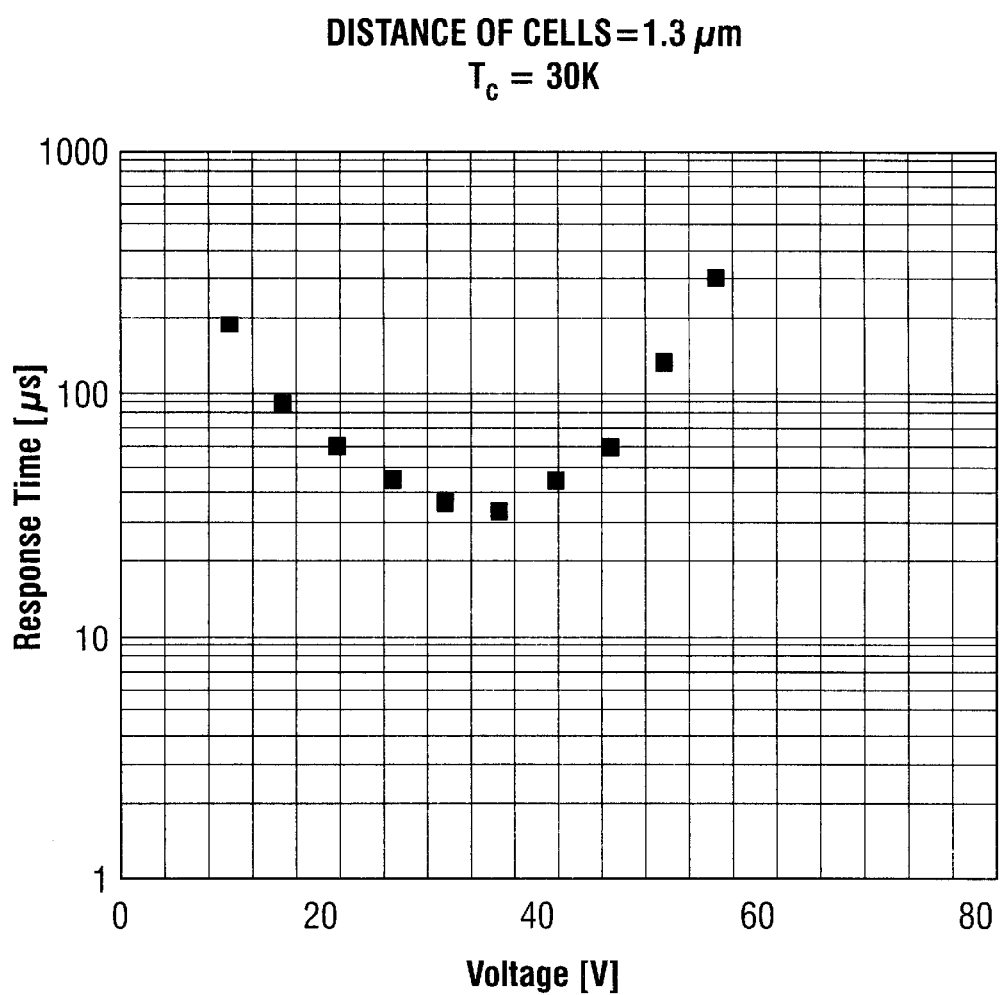
FIG. 1 shows a voltage, response time curve.

It has now been found that these requirements are satisfied by fluorinated polycycles of the formula (I)

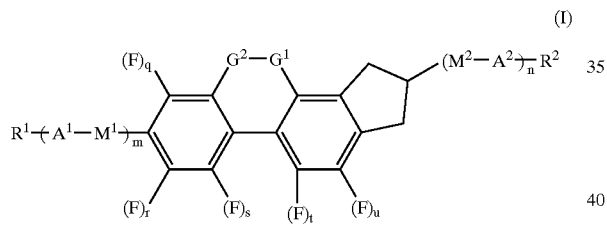

(I)

in which:

R$^1$ is H, F,CF$_3$, OCF$_3$, OCF$_2$H, OCFH$_2$, an alkyl radical having 1 to 12 carbon atoms or an alkenyl radical having 2 to 8 carbon atoms, where, in each case, one (nonterminal) —CH$_2$— group may be replaced by —O— or —C(=O)O— and/or one or more H may be replaced by F;

R$^2$ is H, an alkyl radical or alkyloxy radical having 1 to 12 carbon atoms or an alkenyl or alkenyloxy radical having 2 to 8 carbon atoms, where, in each case, one (nonterminal) —CH$_2$— group may be replaced by —O— or —C(=O)O— and/or one or more H may be replaced by F;

G$^2$—G$^1$ is —CH=CH—, —CH$_2$CH$_2$—, —CF=CH—, —CH=CF—, —CF=CF—, —CH$_2$—, —CF$_2$—;

M$^1$, M$^2$ are each, independently of one another, —C(=O)O—, —OC(=O)—, —CH$_2$O—, —OCH$_2$—, —OCF$_2$—, —CF$_2$O—, —C≡C—, —CH$_2$CH$_2$—, —CF$_2$CF$_2$— or a single bond;

A$^1$, A$^2$ are each, independently of one another, phenylene-1,4-diyl, unsubstituted, monosubstituted or disubstituted by F, cyclohexane-1,4-diyl, 1,3-dioxan-2,5-diyl;

m, n are each, independently of one another, zero or 1; m+n=0 or 1;

q, r, s, t, u are each, independently of one another, zero or 1 with the provisos that a) when G$^2$—G$^1$ is —CF=CH— or —CF=CF—, r, s, t, u must be zero b) when q=1, s and u must be zero c) when G$^2$—G$^1$ is —CH=CH— or —CH$_2$CH$_2$—, at least one of q, r, s, t, u must be 1.

Preference is given to compounds of the formula (I) in which

G$^2$—G$^1$ is —CH=CH— or —CH$_2$CH$_2$—, t and u=1, q=0, r and/or s=0 or 1 and n=0;

G$^2$—G$^1$ is —CH=CH— or —CH$_2$CH$_2$—, s and u=0, q and r=1, t=0 or 1 and n=0;

G$^2$—G$^1$ is —CF=CF— or —CF=CH—, r, s, t and u=0, q=0 or 1 and n=0;

G$^2$—G$^1$ is —CH$_2$—, t and u=1, q=0, r and/or s=0 or 1 and n=0 or

G$^2$—G$^1$ is —CH$_2$—, s and u=0,q and r=1, t=0 or 1 and n=0.

Particular preference is given to the compounds of the formulae (Ia) to (Im)

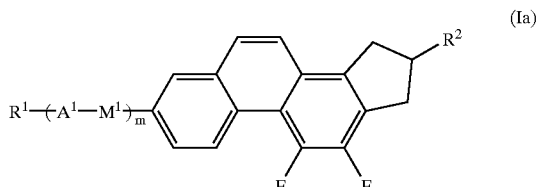
(Ia)

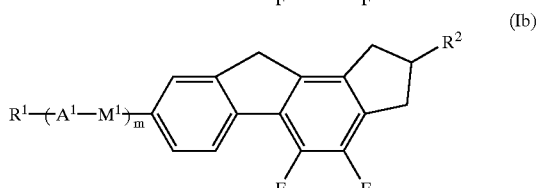
(Ib)

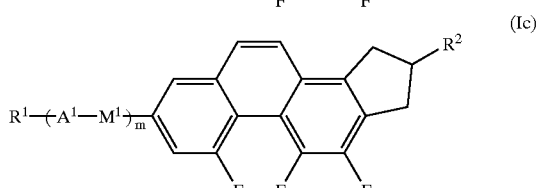
(Ic)

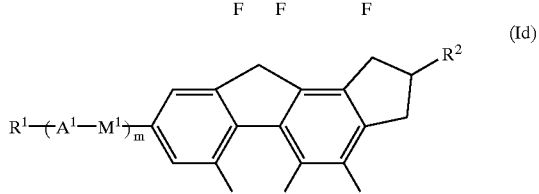
(Id)

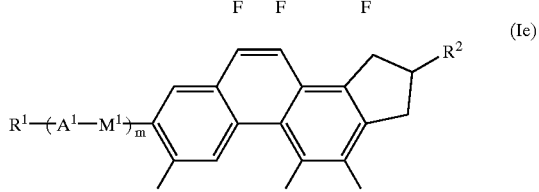
(Ie)

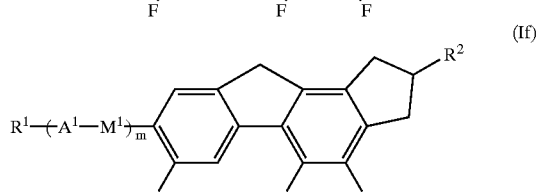
(If)

-continued

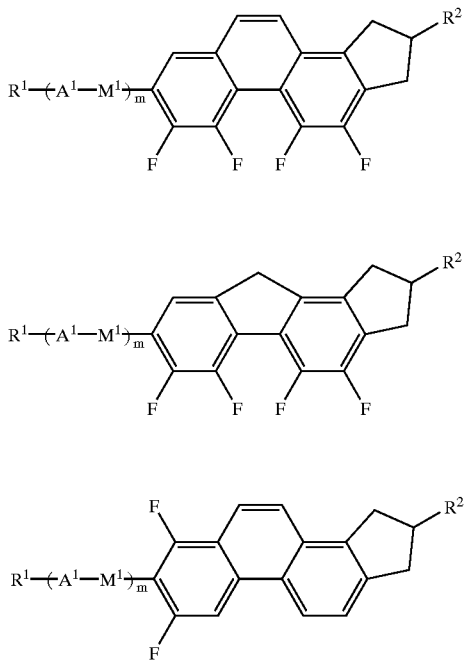

Here and hereinbelow, (Ii) shall also encompass the isomeric compound of the formula (Iia) which is also formed in the cyclization reaction e) (cf. scheme 5); and furthermore mixtures of (Ii) and (Iia).

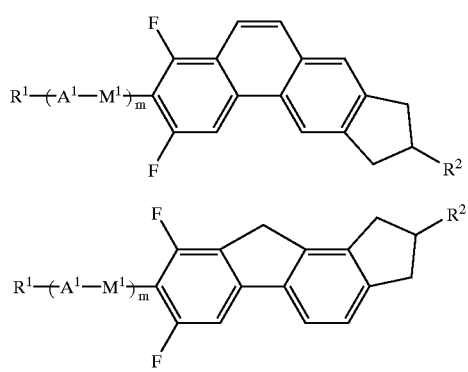

Here and hereinbelow, (Ij) shall also encompass the isomeric compound of the formula (Ija) which is also formed in the cyclization reaction e) (cf. scheme 5); and furthermore mixtures of (Ij) and (Ija)

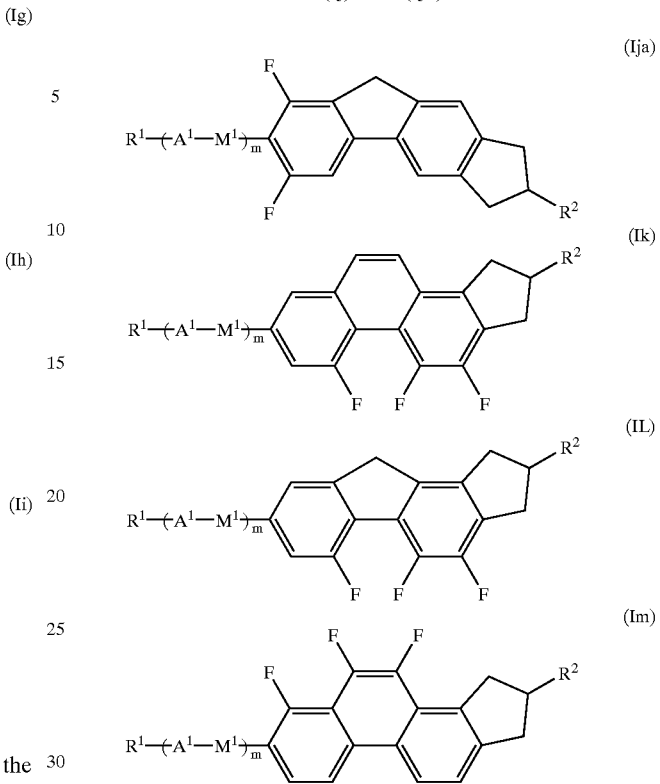

Particular preference is given to compounds of the formula (IB)

in which $R^3$=F, $OCF_3$, $CF_3$, $OF_2H$ or $OCFH_2$, t=zero or 1 and $R^2$ is an alkyl radical or alkyloxy radical having 1 to 12 carbon atoms or an alkenyl or alkenyloxy radical having 2 to 8 carbon atoms, where, in each case, one (nonterminal) —$CH_2$— group may be replaced by —O— or —C(=O)O—.

The compounds (Ia) and (Ib) are synthesized as shown in scheme 1:

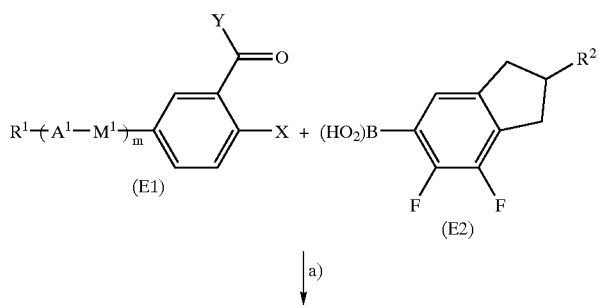

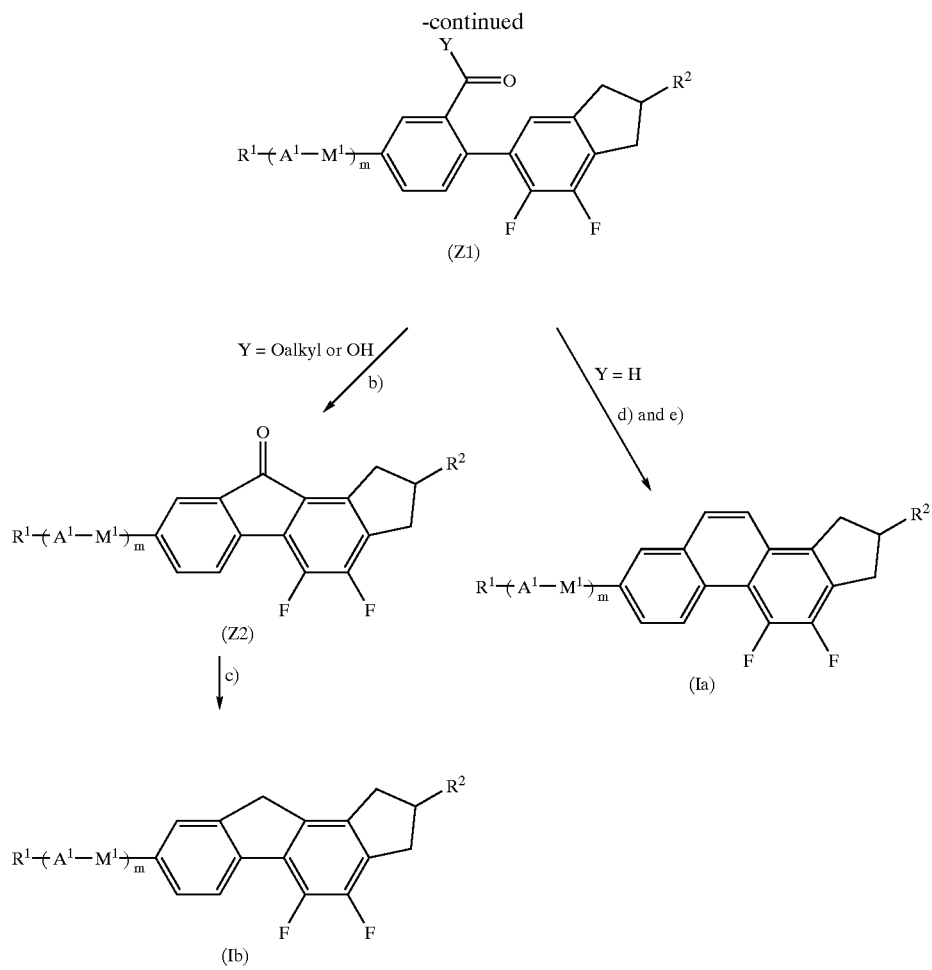

(E1) For compounds in which m is zero, the following starting materials are known from the literature:

Y=H X=OH

R$^1$=methyl [613-84-3], ethyl [52411-3-5], propyl [81323-69-5], butyl [77635-19-9], pentyl [92954-31-9], hexyl [18102-14-2], octyl [73318-92-0], nonyl [63753-10-6].

R$^1$=methyloxy [672-13-9], ethyloxy [80832-54-8], propyloxy [179728-35-9], butyloxy [41002-38-4], pentyloxy [291507-15-8], hexyloxy [291507-16-9], heptyloxy [291507-17-0], octyloxy [165614-97-1]. In all cases, the OH group must be converted into the corresponding triflate—which is the active component (E1) of reaction step a)—by reaction with trifluoromethanesulfonic anhydride.

Y=H X=Br

These bromo compounds are an alternative to the above-mentioned phenols; for instance, R$^1$=methyl [90221-55-9] is known, the homologs can be obtained in a similar manner.

R$^1$=methyloxy [7507-86-0], ethyloxy [43192-32-1], propyloxy [195005-37-9].

Y=O-alkyl or OH X=Br or I

In this case, R$^1$=methyl, Y=O-methyl, X=Br [35450-36-3]; R$^1$=methyloxy, Y=OH, X=Br [22921-68-2]; R$^1$=butyloxy, Y=OH, X=I [114185-61-4] are known from the literature.

Compounds (E1) in which m=1 can likewise be used in reaction step a) (obtainable, for example, by reacting the "mesogenic" phenol with hexamethylenetetraamine in trifluoroacetic acid, as described in DE-A-19921318).

It is likewise possible to employ (E1) as a methoxy compound (R$^1$=methoxy, m=0) and to perform an ether cleavage (for example using HBr/acetic acid or BBr$_3$) in the final step (Ia) or (Ib); the resulting phenol (M$^1$=single bond) can be converted into the triflate and thus be reacted with "mesogenic" boronic acids in a Suzuki reaction; furthermore the phenol (M$^1$=—C(=O)O—) can also be reacted with "mesogenic" carboxylic acids. It is also possible to perform further derivatizations known to the person skilled in the art which give (Ia) or (Ib) where m=1. In this context, "mesogenic" is intended to mean well-known building blocks of liquid-crystal compounds which typically have a para (alkyl) substituent on a phenyl ring [which may or may not have further substituents including rings, such as cyclohexane, in a suitable (e.g. para) position].

(E2) is known from DE-A-19840447.

The individual reaction steps can be performed similarly to the methods described in the following references which are incorporated herein by reference.

a) Pd catalyst, CsF, DME Kumar, J.Org.Chem. 62, 8535 (1997)

b) (Y=OH) 1. SOCl$_2$ 2. AlCl$_3$ DE-A 10101021 c) Et$_3$SiH, TFA Nagai, Org.Prep.Proc.Int. 12, 15 (1980)

d) Me$_3$S$^+$I$^-$, base Kumar, J.Org.Chem. 62, 8535 (1997)

e) BF$_3$-Et$_2$O Kumar, J.Org.Chem. 62, 8535 (1997)

The compounds (Ic) and (Id) can be synthesized in accordance with scheme 2.

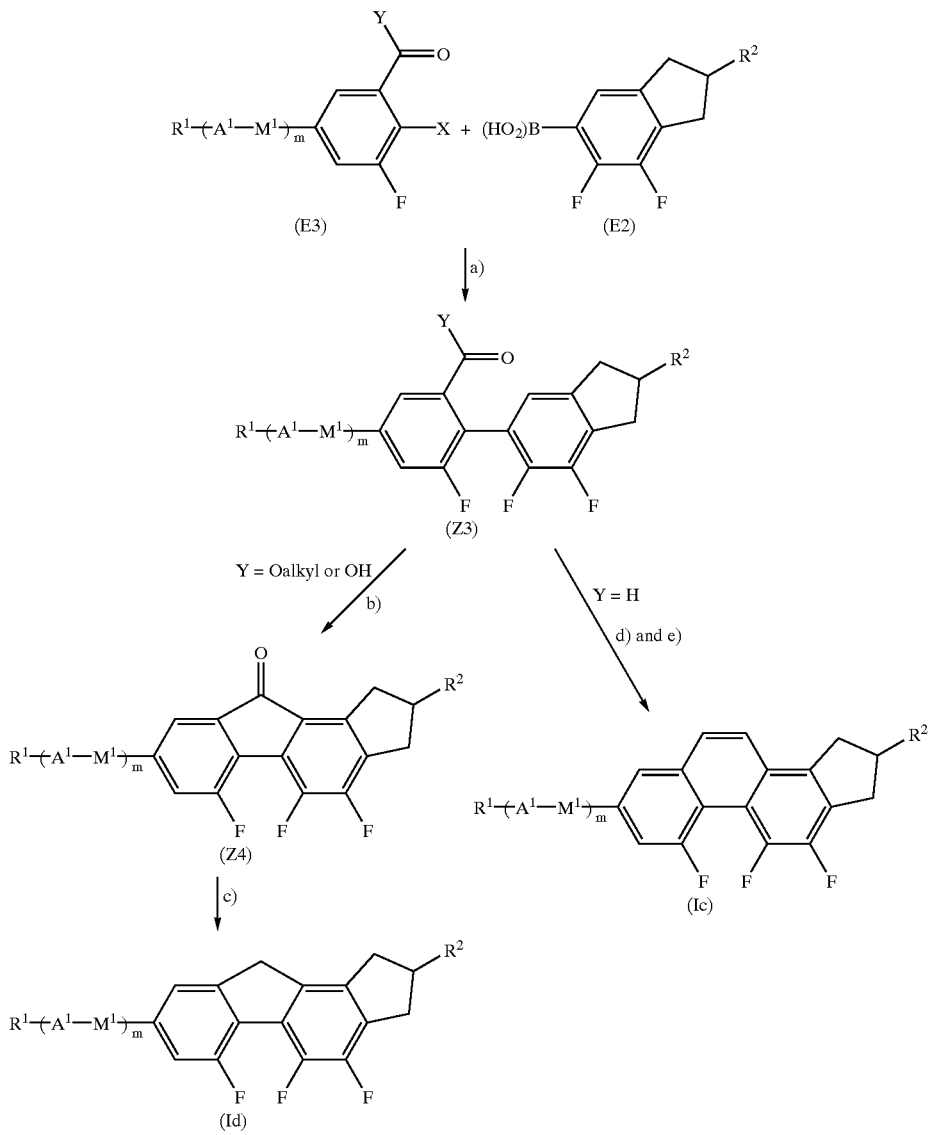

Scheme 2

(E3): The following starting materials are suitable for compounds in which m=zero:

Y=H; X=OH

These compounds can be obtained by ortho formylation (similarly to the method described in: J.Chem.Soc. Perkin Trans 1 1994, 1823) of the following compounds, known from the literature, of the type

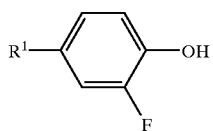

$R^1$=methyl [451-81-3], ethyl [326493-66-7], propyl [80222-25-9], butyl [80222-26-0], pentyl [78322-87-9], hexyl [80222-27-1], heptyl [80222-28-2], octyl [80222-29-3]; further homologs can be prepared in a similar manner.

$R^1$=methoxy [167683-93-4]; further homologs can be prepared in a similar manner.

Y=OH; X=OH

These compounds can be prepared by oxidation (e.g. using $Ag_2O$ similarly to the method described in Org.Synth.Coll.Vol.4, 919 (1963)) of the compounds (E3) in which Y=H.

In all cases, the OH group must be converted into the corresponding triflate—which is the active component (E3) of reaction step a)—by reaction with trifluoromethane-sulfonic anhydride.

Compounds (E3) in which m=1 can likewise be used in reaction step a); it is likewise possible to employ (E3) as a methoxy compound and to perform an ether cleavage (for example using HBr/acetic acid or $BBr_3$) in the final step (Ic) or (Id); the resulting phenol ($M^1$=single bond) can be converted into the triflate and thus be reacted with "mesogenic" boronic acids in a Suzuki reaction; furthermore the phenol ($M^1$=—C(=O)O—) can also be reacted with "mesogenic" carboxylic acids. It is also possible to perform further derivatizations known to the person skilled in the art which give (Ic) or (Id) where m=1.

The compounds (Ie) and (If) can be synthesized in accordance with scheme 3.

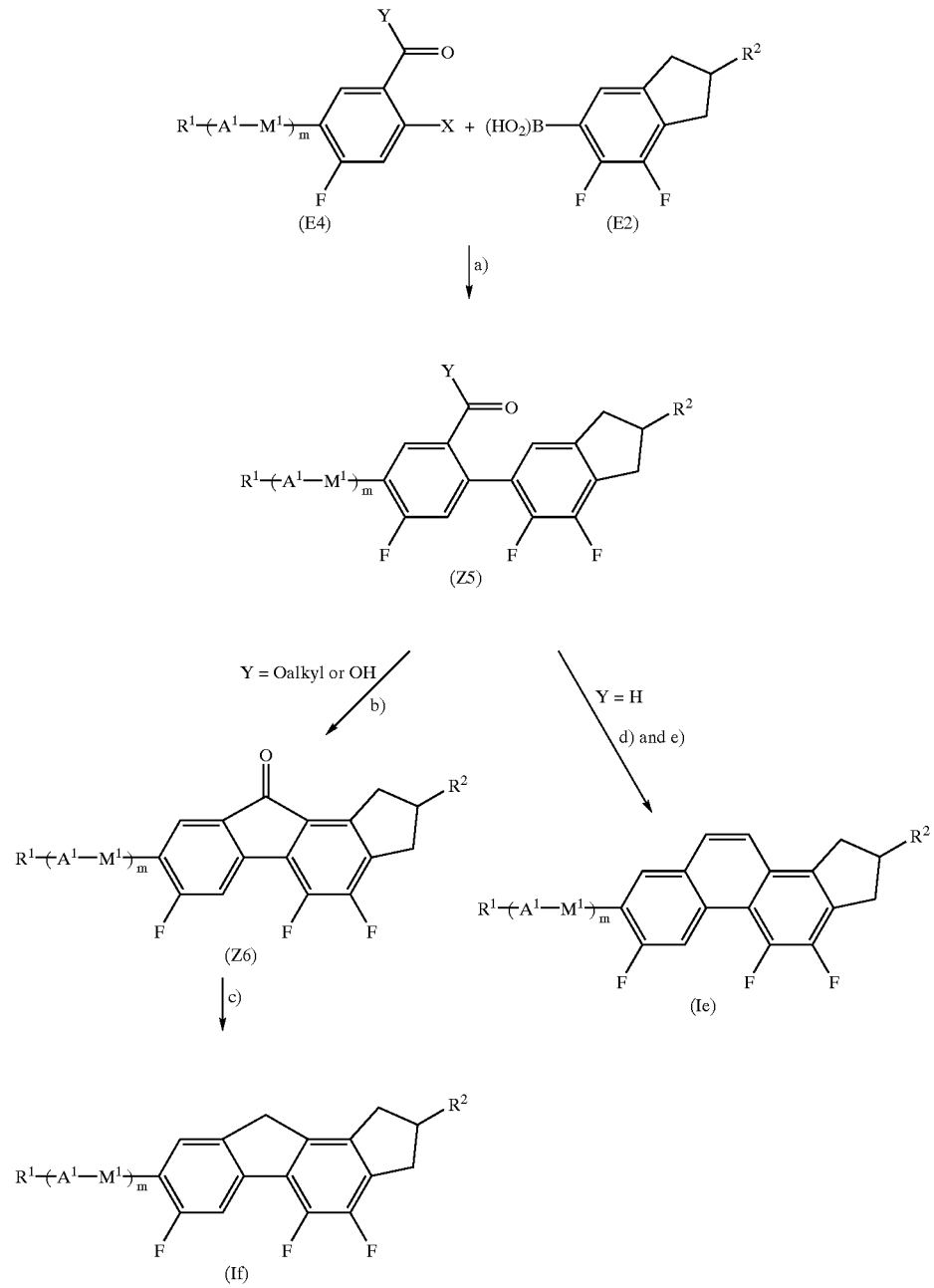

The individual reaction steps can be performed similarly to the methods described in the following references which are incorporated herein by reference.
a) Pd catalyst, CsF, DME Kumar, J.Org.Chem. 62, 8535 (1997)
b) (Y=OH) 1. $SOCl_2$ 2. $AlCl_3$ DE-A 10101021
c) $Et_3SiH$, TFA Nagai, Org.Prep.Proc.Int. 12, 15 (1980)
d) $Me_3S^+I^-$, base Kumar, J.Org.Chem. 62, 8535 (1997)
e) $BF_3$-$Et_2O$ Kumar, J.Org.Chem. 62, 8535 (1997)

(E4) The following starting materials are known for compounds in which m=zero:
Y=H; X=Cl
$R^1$=methoxy [177034-23-0]; further homologs can be prepared similarly to the methoxy compound (WO 96/02485).
Y=H; X=OH
$R^1$=octyloxy [161987-33-3]; undecyloxy [161987-34-4]; further homologs can be prepared in a similar manner. (Blake, Inorg.Chem. 34 (5), 1125 (1995)).
Y=OH; X=OH These compounds can be prepared by oxidation (e.g. using Ag$_2$O similarly to the method described in Org.Synth.Coll.Vol.4, 919 (1963)) of the compounds (E4) in which Y=H.

In all cases, the OH group must be converted into the corresponding triflate—which is the active component (E4) of reaction step a)—by reaction with trifluoromethanesulfonic anhydride.

Compounds (E4) in which m=1 can likewise be used in reaction step a); it is likewise possible to employ (E4) as an alkoxy compound and to perform an ether cleavage (for example using HBr/acetic acid or BBr$_3$) in the final step (Ie) or (If); the resulting phenol (M$^1$=single bond) can be converted into the triflate and thus be reacted with "mesogenic" boronic acids in a Suzuki reaction; furthermore the phenol (M$^1$=—C(=O)O—) can also be reacted with "mesogenic" carboxylic acids. It is also possible to perform further derivatizations known to the person skilled in the art which give (Ie) or (If) where m=1.

The individual reaction steps can be performed similarly to the methods described in the following references.
a) Pd catalyst, CsF, DME Kumar, J.Org.Chem. 62, 8535 (1997)
b) (Y=OH) 1. SOCl$_2$ 2. AlCl$_3$ DE-A 10101021
c) Et$_3$SiH, TFA Nagai, Org.Prep.Proc.Int. 12, 15 (1980)
d) Me$_3$S$^+$I$^-$, base Kumar, J.Org.Chem. 62, 8535 (1997)
e) BF$_3$-Et$_2$O Kumar, J.Org.Chem. 62, 8535 (1997)

The compounds (Ig) and (Ih) can be synthesized in accordance with scheme 4.

Scheme 4

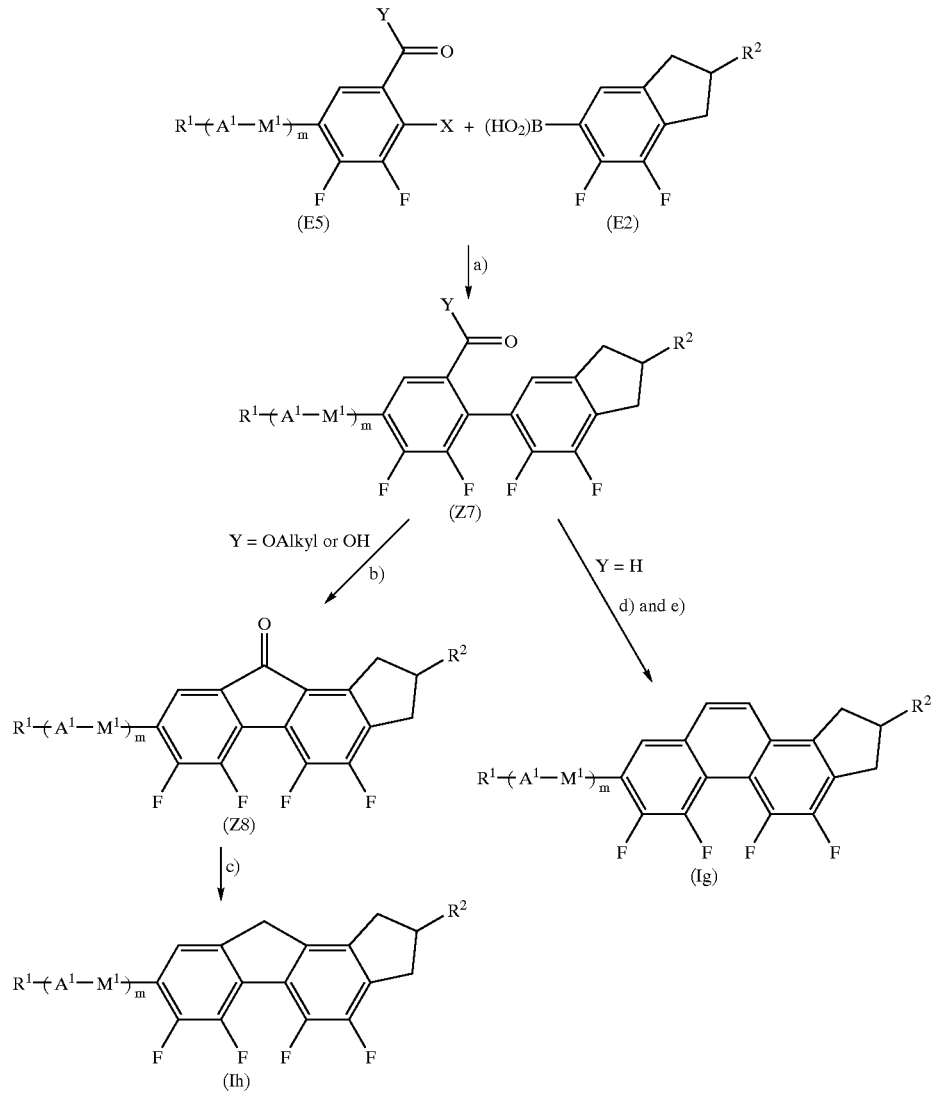

(E5): The following starting materials are suitable for compounds in which m=zero:

Y=H; X=OH

These compounds can be obtained by ortho formylation (similarly to the method described in: J.Chem.Soc. Perkin Trans 1 1994, 1823) of the following compounds, known from the literature, of the type

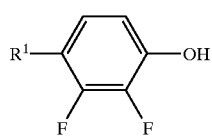

$R^1$=methyl [261763-43-5]; ethyl [124728-38-7], propyl [124728-91-2], pentyl [126163-37-9]; further homologs can be prepared in a similar manner.

$R^1$=methoxy [261763-29-5]; ethoxy [126163-56-2], butoxy [136239-68-4]; further homologs can be prepared in a similar manner.

Y=OH; X=OH

These compounds can be prepared by oxidation (e.g. using $Ag_2O$ similarly to the method described in Org.Synth.Coll.Vol.4, 919 (1963)) of the compounds (E4) in which Y=H.

In all cases, the OH group must be converted into the corresponding triflate—which is the active component (E5) of reaction step a)—by reaction with trifluoromethane-sulfonic anhydride.

Compounds (E5) in which m=1 can likewise be used in reaction step a); it is likewise possible to employ (E5) as an alkoxy compound and to perform an ether cleavage (for example using HBr/acetic acid or $BBr_3$) in the final step (Ig) or (Ih); the resulting phenol ($M^1$=single bond) can be converted into the triflate and thus be reacted with "mesogenic" boronic acids in a Suzuki reaction; furthermore the phenol ($M^1$=—C(=O)O—) can also be reacted with "mesogenic" carboxylic acids. It is also possible to perform further derivatizations known to the person skilled in the art which give (Ig) or (Ih) where m=1.

The individual reaction steps can be performed similarly to the methods described in the following references.

a) Pd catalyst, CsF, DME Kumar, J.Org.Chem. 62, 8535 (1997)

b) (Y=OH) 1. $SOCl_2$ 2. $AlCl_3$ DE-A 10101021 c) $Et_3SiH$, TFA Nagai, Org.Prep.Proc.Int. 12, 15 (1980)

d) $Me_3S^+I^-$, base Kumar, J.Org.Chem. 62, 8535 (1997)

e) $BF_3$-$Et_2O$ Kumar, J.Org.Chem. 62, 8535 (1997)

The compounds (Ii) and (Ij) can be synthesized in accordance with scheme 5.

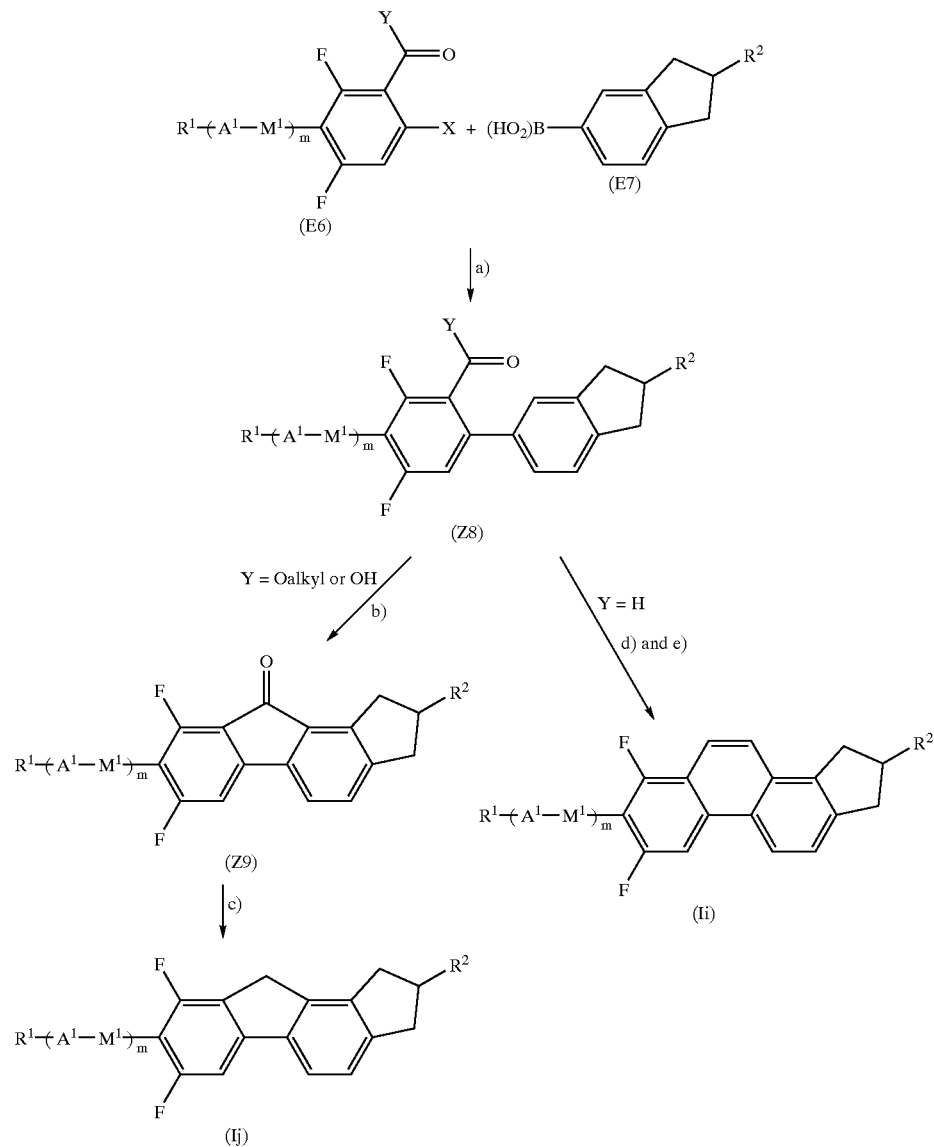

(E6) The following starting materials are suitable for compounds in which m=zero:

Y=OH X=Br $R^1$=methoxy [250351-78-1]; homologs can be prepared similarly to the method described in WO 99/58521.

Y=H; X=OH

These compounds can be prepared by reduction (e.g. Rosenmund reduction similarly to the method described in J.Am.Chem.Soc. 108, 2608 (1986)) of those compounds (E6) in which Y=OH.

The OH group must be converted into the corresponding triflate—which is the active component (E6) of reaction step a)—by reaction with trifluoromethanesulfonic anhydride.

Compounds (E6) in which m=1 can likewise be used in reaction step a); it is likewise possible to employ (E6) as an alkoxy compound and to perform an ether cleavage (for example using HBr/acetic acid or $BBr_3$) in the final step (Ii) or (Ij); the resulting phenol ($M^1$=single bond) can be converted into the triflate and thus be reacted with "mesogenic" boronic acids in a Suzuki reaction; furthermore the phenol ($M^1$=—C(=O)O—) can also be reacted with "mesogenic" carboxylic acids. It is also possible to perform further derivatizations known to the person skilled in the art which give (Ii) or (Ij) where m=1.

(E7) can be prepared similarly to the method decribed in EP-A-0546338.

The individual reaction steps can be performed similarly to the methods described in the following references.

a) Pd catalyst, CsF, DME Kumar, J.Org.Chem. 62, 8535 (1997)

b) (Y=OH) 1. $SOCl_2$ 2. $AlCl_3$ DE-A 10101021 c) $Et_3SiH$, TFA Nagai, Org.Prep.Proc.Int. 12, 15 (1980)

d) $Me_3S^+I^-$, base Kumar, J.Org.Chem. 62, 8535 (1997)

e) $BF_3$-$Et_2O$ Kumar, J.Org.Chem. 62, 8535 (1997)

The compounds of the formula (I) are preferably used in nematic or cholesteric liquid-crystal mixtures. The liquid-crystal mixtures of the invention comprise at least one compound of the formula (I), preferably in an amount of 1 to 40% by weight, based on the liquid-crystal mixture.

They preferably comprise at least 3 further components. The selection of these further compounds (e.g. from the types listed in DE-A-196 29 812, p.12 to 16) and the preparation of the liquid-crystal mixtures are known to the person skilled in the art.

The invention furthermore provides a liquid-crystal display containing these liquid-crystal mixtures. This liquid-crystal display preferably operates in IPS display mode (Kiefer et al., Japan Display '92, p. 547) or in VA diplay mode (Ohmura et al., SID 97 Digest, p. 845) or in ECB display mode (EP-A-0 474 062).

Preference is likewise given to using the compounds of the formula (I) in chiral smectic liquid-crystal mixtures. The liquid-crystal mixtures of the invention comprise at least one compound of the formula (I), preferably in an amount of 1 to 40% by weight, based on the liquid-crystal mixture. They preferably comprise at least 3 further components. The selection of these further compounds (e.g. from the types listed in DE-A-198 57 352) and the preparation of the liquid-crystal mixtures are known to the person skilled in the art.

The invention furthermore provides a liquid-crystal display containing these liquid-crystal mixtures. This liquid-crystal display preferably operates in inverse mode (e.g."Fast High Contrast Ferroelectric Liquid Crystal Displays and the Role of Dielectric Biaxiality" by J. C. Jones, M. J. Towler, J. R. Hughes, Displays, Volume 14, No. 2(1993) 86–93 or M. Koden, Ferroelectrics 179, 121(1996)).

The examples which follow illustrate the invention in more detail.

EXAMPLE 1

11,12-Difluoro-3-pentyl-16-propyl-16,17-dihydro-15H-cyclopenta[a]phenanthrene [(I)), m, n=0; q, r, s=0; t, u=1; $G^2$—$G^1$=—CH=CH—; $R^1$=pentyl, $R^2$=propyl]

A mixture of 6.5 g (20 mmol) of 2-trifluoromethylsulfonyloxy-5-pentylbenzaldehyde (scheme 1:E1 in which m=0, $R^1$=pentyl, Y=H, X=$OSO_2CF_3$), 4.8 g (20 mmol) of (4,5-difluoro-2-propyl) indane-6-boronic acid (scheme 1:E2 in which $R^2$=propyl), 3 g (20 mmol) of cesium fluoride and 50 ml of dimethoxy-ethane was treated with 0.3 g of tetrakis(triphenylphosphine) palladium(0) and refluxed for 28 h. The mixture was cooled down to room temperature, water and tert-butyl methyl ether were added, the organic phase was separated off, the aqueous phase was extracted with tert-butyl methyl ether, and the organic phases were combined, washed with saturated sodium cholride solution and evaporated to dryness under reduced pressure. The dark oil was filtered through 500 g of $SiO_2$ using about 1.5 l of dichloromethane. Evaporation gave 3.6 g of raw product {4,5-difluoro-6-(2-formyl-4-pentylphenyl)-2-propyl-indane (scheme 1: Z1 in which m=0, $R^1$=pentyl, $R^2$=propyl, Y=H) which were dissolved in 80 ml of dichloromethane, treated with 30 ml of 50% strength aqueous sodium hydroxide solution, 4 g (19.8 mmol) of trimethylsulfonium iodide and 50 mg of tetrabutylammonium iodide and refluxed until the reaction was complete (TLC monitoring). The mixture was poured into ice/water, the organic phase was separated off, the aqueous phase was extracted with dichloromethane, the organic phases were combined and dried with sodium sulfate. 10 ml of methanesulfonic acid were added dropwise to this solution of the raw product {4,5-difluoro-6-[2-(oxiran-2-yl)-4-pentylphenyl]-2-propyl-indane} over the course of 5 minutes with cooling. After the reaction was complete, the mixture was poured onto four times the amount of ice-cold 10% strength aqueous sodium hydroxide solution. The organic phase was separated off, washed with water and dried, and the solvent was removed by distillation under reduced pressure. The residue was chromatographed over 50 times the amount of silica gel using toluene. Product-containing fractions were combined, the solvent was removed by distillation and the residue was recrystallized from acetonitrile; 1.5 g of product, m.p. 61–64° C.

EXAMPLE 2

11,12-Difluoro-3-pentyl-16-propyl-6,7,16,17-tetrahydro-15H-cyclopenta[a]phenanthrene [(I)), m, n=0; q, r, s=0; t, u=1; $G^2$—$G^1$=—$CH_2CH_2$—; $R^1$=pentyl, $R^2$=propyl]

A solution of 0.5 g of the compound from Example 1 in 20 ml of tetrahydrofuran was treated with 0.1 g of palladium (5% on activated carbon) and hydrogenated at atmospheric pressure and room temperature until no more hydrogen was absorbed. The mixture was then filtered through Celite, the filtrate was evaporated to dryness under reduced pressure, the residue was chromatographed over 20 times the amount of silica gel using toluene, the eluate was evaporated and the residue was recrystallized from acetonitrile; 0.3 g of a viscous oil.

EXAMPLE 3

4,5-Difluoro-8-pentyl-2-propyl-1,2,3,10-tetrahydro-cyclopenta[a]fluorene [(I)), m, n=0; q, r, s=0; t, u=1; $G^2$—$G^1$=—$CH_2$—; $R^1$=pentyl, $R^2$=propyl]

A solution of 4.8 g of the raw product {4,5-difluoro-6-(2-formyl-4-pentyl)phenyl-2-propyl-indane from Example 1 in 50 ml of ethanol was treated with a solution of 4.8 g of silver nitrate in 15 ml of water; subsequently a solution of 2.6 g of sodium hydroxide in 7 ml of water was added dropwise over the course of 30 min and stirring was continued for another 4 h at room temperature. The mixture was filtered and the filtrate was adjusted to pH 1 by adding half-concentrated hydrochloric acid, the precipitate is collected by filtration and dried by taking it up in dichloromethane and adding sodium sulfate. Removal of the dichloromethane gave the raw product {4,5-difluoro-6-(2-carboxyl-4-pentylphenyl)-2-propyl-indane (scheme 1: Z1 in which m=0, $R^1$pentyl, $R^2$=propyl, Y=OH) which was treated with 10 times the amount of thionyl chloride and heated until gas evolution had ceased; excess thionyl chloride was removed by distillation under reduced pressure, near the end by co-distilling with toluene. The raw product {4,5-difluoro-6-(2-chlorcarbonyl-4-pentyl )phenyl-2-propyl-indane) (scheme 1: Z1 in which m=0, $R^1$=pentyl, $R^2$=propyl, Y=Cl) was dissolved in 50 ml of dichloromethane and added dropwise over the course of 1 hour to a suspension of 2.4 g of aluminum chloride in 150 ml of dichloromethane at a temperature of 0 to 5° C. The mixture was then poured onto 1 l of ice water, the resulting mixture was extracted with 200 ml of dichloromethane, the extract was washed with water and dried with sodium sulfate. The solvent was removed by distillation and the residue was chromatographed over 50 times the amount of silica gel using toluene. Product-containing fractions were combined and the solvent was removed by distillation. The residue ((scheme 1: Z2 in which m=0, $R^1$=pentyl, $R^2$=propyl) was dissolved in 30 ml of trifluoroacetic acid, 7 g of triethylsilane were added with cooling and the mixture was refluxed until the reaction was complete. The mixture was poured onto 10 times the amount of ice water, the resulting mixture was extracted with 100 ml of dichloromethane, the extract was washed to neutrality with water and dried with sodium sulfate. The solvent was removed by distillation and the residue was chromatographed over 50 times the amount of silica gel using toluene. Product-containing fractions were combined and the solvent was removed by distillation. The residue was recrystallized from acetonitrile; 1.1 g of a viscous oil.

EXAMPLE 4

A chiral smectic liquid-crystal mixture M1 having a melting point of 7° C. is admixed with 10% by weight of the compound from Example 1. The resulting mixture has a melting point of 0° C. The voltage/response time curve (FIG. 1) has the minimum required for inverse mode operation, the values achieved are within the industrially relevant range and the mixture is suitable for practical use.

EXAMPLE 5

A chiral smectic liquid-crystal mixture M2 (consisting of a plurality of phenylpyrimidine and 2,3-difluorophenylpyrimidine derivatives) having a melting point of 7° C. is admixed with 15% by weight of the compound from Example 1. The resulting mixture has a melting point of −2°0 C. As a result of adding the compound of the invention, the dielectric anisotropy (Δε) has changed from −0.65 to −0.8.

What is claimed is:

1. A compound of the formula (I)

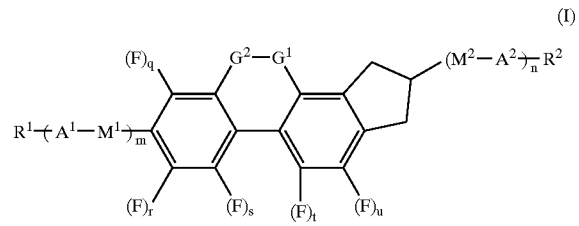

(I)

in which:

$R^1$ is H, F, $CF_3$, $OCF_3$, $OCF_2H$, $OCFH_2$, an alkyl radical having 1 to 12 carbon atoms or an alkenyl radical having 2 to 8 carbon atoms, where, in each case, one (nonterminal) —$CH_2$— group may be replaced by —O— or —C(=O)O— and/or one or more H may be replaced by F;

$R^2$ is H, an alkyl radical or alkyloxy radical having 1 to 12 carbon atoms or an alkenyl or alkenyloxy radical having 2 to 8 carbon atoms, where, in each case, one (nonterminal) —$CH_2$— group may be replaced by —O— or —C(=O)O— and/or one or more H may be replaced by F;

$G^2$—$G^1$ is —CH=CH—, —$CH_2CH_2$—, —CF=CH—, —CH=CF—, —CF=CF—, —$CH_2$—, —$CF_2$—;

$M^1$, $M^2$ are each, independently of one another, —C(=O)O—, —OC(=O)—, —$CH_2O$—, —$OCH_2$—, —$OCF_2$—, —$CF_2O$—, —C≡C—, —$CH_2CH_2$—, —$CF_2CF_2$— or a single bond;

$A^1$, $A^2$ are each, independently of one another, phenylene-1,4-diyl, unsubstituted, monosubstituted or disubstituted by F, cyclohexane-1,4-diyl, 1,3-dioxan-2,5-diyl;

m, n are each, independently of one another, zero or 1; m+n=0 or 1; with the provisos that a) when $G^2$—$G^1$ is —CF=CH— or —CF=CF—, r, s, t, u must be zero
b) when q=1, s and u must be zero
c) when $G^2$—$G^1$ is —CH=CH— or —$CH_2CH_2$—, at least one of q, r, s, t, u must be 1.

2. A compound as claimed in claim 1, wherein the compounds of the formula (I) correspond to the compounds of the formulae (Ia) to (Ii)

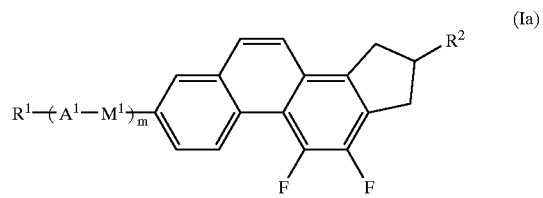

(Ia)

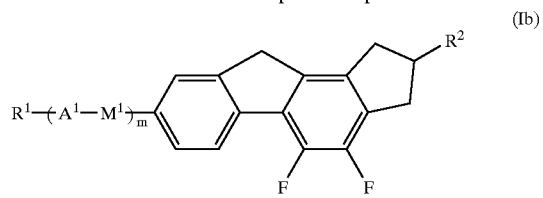

(Ib)

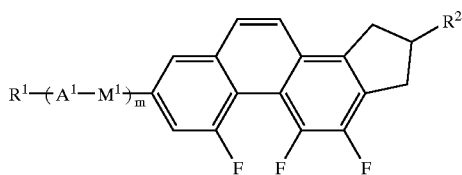 (Ic)

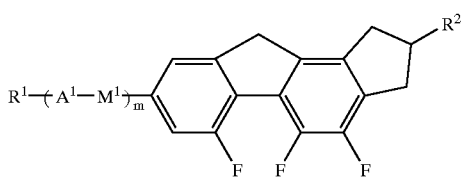 (Id)

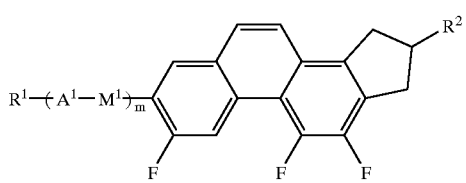 (Ie)

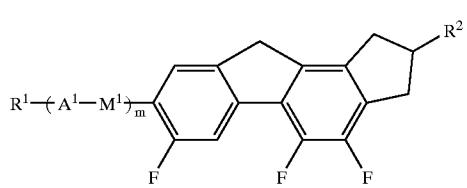 (If)

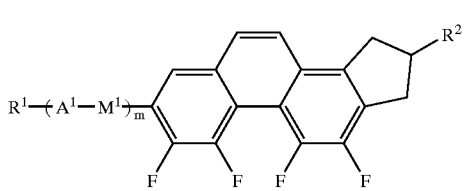 (Ig)

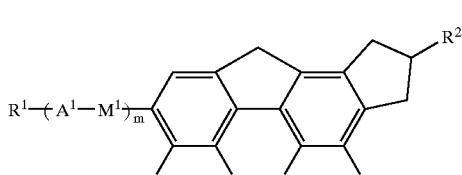 (Ih)

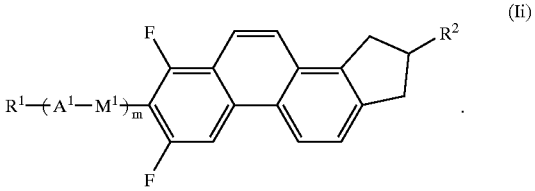 (Ii)

3. A compound as claimed in claim 1, wherein, in the formula (I), $G^2$—$G^1$ is —CH=CH— or —CH$_2$CH$_2$—, t and u=1, q=0, r and/or s=0 or 1 and n=0.

4. A compound as claimed in claim 1, wherein, in the formula (I), $G^2$—$G^1$ is —CH=CH— or —CH$_2$CH$_2$—, s and u=0, q and r=1, t=0 or 1 and n=0.

5. A compound as claimed in claim 1, wherein, in the formula (I), $G^2$—$G^1$ is —CF=CF— or —CF=CH—, r, s, t and u=0, q=0 or 1 and n=0.

6. A compound as claimed in claim 1, wherein, in the formula (I), $G^2$—$G^1$ is —CH$_2$—, t and u=1, q=0, r and/or s=0 or 1 and n=0.

7. A compound as claimed in claim 1, wherein, in the formula (I), $G^2$—$G^1$ is —CH$_2$—, s and u=0, q and r=1, t=0 or 1 and n=0.

8. A liquid-crystal mixture which comprises a compound of the formula (I) as claimed in claim 1.

9. A liquid-crystal mixture comprising one or more compounds as claimed in claim 1 in an amount of 1 to 40% by weight, based on the liquid-crystal mixture.

10. A liquid-crystal mixture as claimed in claim 9, which is chiral smectic.

11. A liquid-crystal mixture as claimed in claim 9, which is nematic or cholesteric.

12. A liquid-crystal display containing a liquid-crystal mixture as claimed in claim 9.

13. A liquid-crystal display as claimed in claim 12 which is operated in ECB, IPS or VA display mode.

14. A liquid-crystal display as claimed in claim 12 which is operated in inverse mode.

15. A liquid-crystal display containing a liquid-crystal mixture as claimed in claim 11.

16. A liquid-crystal mixture which comprises a compound of the formula (I) as claimed in claim 2.

17. A liquid-crystal mixture comprising one or more compounds as claimed in claim 2 in an amount of 1 to 40% by weight, based on the liquid-crystal mixture.

* * * * *